(12) United States Patent
Keller

(10) Patent No.: US 11,547,586 B2
(45) Date of Patent: Jan. 10, 2023

(54) CATHETER DEVICE WITH AN IMPLANT CAPSULE ATTACHED VIA TABS

(71) Applicant: BIOTRONIK AG, Buelach (CH)

(72) Inventor: Mark Keller, Aarau (CH)

(73) Assignee: BIOTRONIK AG, Buelach (CH)

( * ) Notice: Subject to any disclaimer, the term of this patent is extended or adjusted under 35 U.S.C. 154(b) by 687 days.

(21) Appl. No.: 16/089,490

(22) PCT Filed: Mar. 30, 2017

(86) PCT No.: PCT/EP2017/057503
§ 371 (c)(1),
(2) Date: Aug. 24, 2020

(87) PCT Pub. No.: WO2017/167857
PCT Pub. Date: Oct. 5, 2017

(65) Prior Publication Data
US 2020/0390576 A1    Dec. 17, 2020

(30) Foreign Application Priority Data

Mar. 30, 2016  (EP) .................................... 16162862

(51) Int. Cl.
*A61F 2/966*    (2013.01)
*A61F 2/962*    (2013.01)
(Continued)

(52) U.S. Cl.
CPC ............ *A61F 2/966* (2013.01); *A61F 2/2427* (2013.01); *A61F 2/9522* (2020.05); *A61F 2/962* (2013.01);
(Continued)

(58) Field of Classification Search
CPC ...... A61F 2/966; A61F 2/9522; A61F 2/2427; A61F 2002/9505; A61F 2/2436;
(Continued)

(56) References Cited

U.S. PATENT DOCUMENTS 6,936,058 B2 *   8/2005  Forde ...................... A61F 2/962
                                                606/200
2003/0225445 A1 * 12/2003 Derus ....................... A61F 2/95
                                                623/1.11

(Continued)

FOREIGN PATENT DOCUMENTS

WO        199301768 A1    2/1993
WO       2013066883 A1    5/2013

OTHER PUBLICATIONS

Geuer,Melanie International Search Report for Application No. PCT/EP2017/057503, dated Apr. 7, 2017, 20 pages.

*Primary Examiner* — Kelly J Bekker
*Assistant Examiner* — Andrew P. Restaino
(74) *Attorney, Agent, or Firm* — Greer, Burns & Crain, Ltd.; Steven P. Fallon

(57) ABSTRACT

A catheter device for transporting an implant to a target location in a body lumen and also for releasing the implant at the target location. The device includes an outer shaft configured to transport the implant to the target location, and an implant capsule configured to receive the implant. The implant capsule has a tubular capsule core, which surrounds the implant prior to the release. The capsule core, at a proximal end of the capsule core, has a plurality of tabs for fixing the capsule core to the outer shaft, which tabs protrude from a tubular portion of the capsule core along an axial direction of the capsule core.

17 Claims, 4 Drawing Sheets

(51) Int. Cl.
*A61F 2/95* (2013.01)
*A61F 2/24* (2006.01)
(52) U.S. Cl.
CPC ................. *A61F 2002/9505* (2013.01); *A61F 2002/9665* (2013.01)
(58) Field of Classification Search
CPC .. A61F 2/962; A61F 2/95; A61F 2/958; A61F 2/9517; A61F 2002/9511; A61M 25/0026; A61M 25/0043; A61M 25/0009
See application file for complete search history.

(56) References Cited

U.S. PATENT DOCUMENTS

| | | | |
|---|---|---|---|
| 2006/0074477 A1 | 4/2006 | Berthiaume | |
| 2014/0081375 A1* | 3/2014 | Bardill | A61F 2/82 623/1.12 |
| 2014/0324164 A1 | 10/2014 | Gross | |
| 2014/0331475 A1* | 11/2014 | Duffy | A61F 2/9525 29/446 |
| 2017/0000606 A1* | 1/2017 | Crisostomo | A61M 25/0009 |

* cited by examiner

CATHETER DEVICE WITH AN IMPLANT CAPSULE ATTACHED VIA TABS

The present invention is in the field of catheter devices used to transport an implant into through a body lumen and release the implant at a target location.

BACKGROUND

Catheter devices of this type are used to transport an implant, for example in the form of a stent or a (for example bioprosthetic) heart valve to a target location in a body lumen of a human or possibly animal patient. Such a catheter device has an inner shaft for supporting the implant, an outer shaft for transporting the implant to the target location, wherein the outer shaft surrounds the inner shaft in cross-section. Furthermore, an implant capsule for receiving the implant is provided on the outer shaft, wherein the implant capsule has a tubular capsule core, which surrounds the implant prior to the release. The implant can be moved out from the implant capsule by displacing the inner shaft relative to the outer shaft and can be released and implanted at the target location. Furthermore, an outermost stabilisation shaft for stabilising the outer shaft can be provided, wherein the outer shaft is arranged displaceably in a lumen of the stabilisation shaft surrounded by the stabilisation shaft.

The implant capsule generally has a capsule core, which for example forms a supporting structure of the implant capsule and is to be suitably fixed to the outer shaft.

For this purpose, solutions are known in which a connection means (connector) in the form of a plastics injection-moulded part is secured to the outer shaft, to which the implant capsule or prosthesis capsule is glued. Solutions are also known in which the implant capsule has a metal core and the end thereof has finger-like extensions, which are then encapsulated in a plastics connector.

These connections based on adhesive bonding, injection moulding, etc. are often very rigid and have a large overall length, which leads to an inhomogeneous bending form of the catheter. In addition, the catheter in this transition region has an unfavourable increased stiffness.

SUMMARY OF THE INVENTION

A preferred embodiment catheter device includes an outer shaft configured to transport the implant to the target location. An implant capsule is configured to receive the implant, and includes a tubular capsule core that surrounds the implant prior to the release. One end of the capsule core includes a plurality of tabs structured to fix the capsule core to the outer shaft. The tabs protrude from a tubular portion of the capsule core along an axial direction of the capsule core. The catheter device can also include an inner shaft mounted displaceably in the outer shaft for supporting the implant, wherein the implant can be guided out from the implant capsule by displacing the outer shaft relative to the inner shaft.

BRIEF DESCRIPTION OF THE DRAWINGS

Further features and advantages of the invention will be explained in the description of drawings of exemplary embodiments of the invention, with reference to the drawings, in which.

DETAILED DESCRIPTION OF THE PREFERRED EMBODIMENTS

Figure 1:
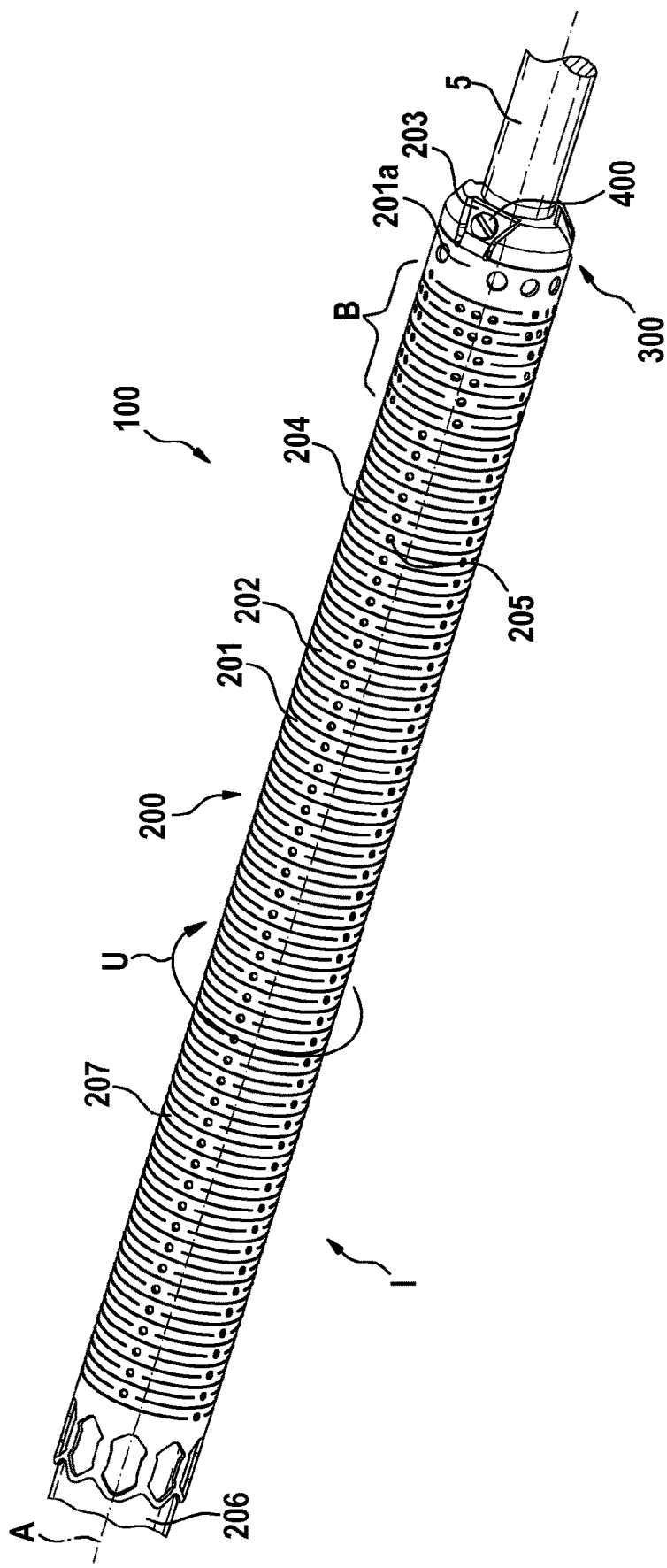
FIG. 1 shows a detail of a catheter device according to the invention.

Preferred embodiment catheters enable a connection of the capsule core to the outer shaft via the tabs, which advantageously provides a sufficient mechanical stability and enables a comparatively short overall length, with which the proportion of the rigid portion can be kept advantageously short.

In the sense of the present invention, "distal" means that a corresponding distal component, a distal portion, or a distal end is distanced further from a handle or an operator (doctor) of the catheter device in the axial direction of the outer shaft, along which the longitudinal axis of the outer shaft extends, than a proximal component, a proximal portion, or a proximal end.

The invention is suitable in particular for a catheter system where the implant is released by a displacement of the outer shaft relative to the inner shaft, in particular where the release is implemented by retracting the outer shaft. In the preferred variant the capsule core then has, at a proximal end of the capsule core, a plurality of tabs for fixing the capsule core to the outer shaft, wherein the tabs protrude from a tubular portion of the capsule core along an axial direction of the capsule core.

The implant capsule can also have an outer covering or material layer arranged on the capsule core, which covering or material layer preferably consists of an elastic or viscoelastic polymer. Here, polymers such as polyurethane or thermoplastic polymers such as thermoplastic copolyamides, for example known under the trade name PEBAX, can be considered as material.

Furthermore, the implant capsule can include an inner covering or material layer surrounded by the capsule core and fixed thereto, which covering or material layer surrounds the actual implant and preferably consists of a plastic having reduced coefficients of friction. In particular, PTFE (also known under the trade name Teflon) or ePTFE or a plastics composite comprising proportions of PTFE or ePTFE is suitable here.

Preferred embodiments include a monolayer implant capsule, which in this case would consist just of the capsule core, which is then referred to as a capsule sleeve. In an embodiment of this type a composite material formed of carbon fibres and a plastic is advantageous, wherein the carbon fibres are integrated in the plastic.

In accordance with a preferred embodiment of the invention, it is also provided that the tabs each have two sides extended along the axial direction, which sides face away from one another in a peripheral direction of the tubular portion, wherein the two sides extend away from one another along the axial direction starting from the tubular portion, such that each tab (starting from the tubular portion) becomes wider accordingly. The tabs are therefore also referred to as dovetails. In this embodiment it is important that the two sides, starting from the tubular portion, extend substantially away from one another. However, the tabs can have small interruptions or indentations, without impairing the function of this embodiment. The widening helps facilitate a good transfer of force.

It is also provided in accordance with one embodiment of the invention that a connector preferably running around the outer shaft is fixed, in particular welded in place, on a distal end portion of the outer shaft, via which connector the tabs are connected to the outer shaft, more specifically preferably by screwing the tabs to the connector. Screwing is the preferred and simplest securing method. It also additionally offers the mechanical advantage that the prestress of the tabs can be determined precisely in combination with the connector. In the case that the connector is milled out accordingly, the lateral flanks of the tabs can be introduced without play into the milled-out area. The tab is tensioned by the screwed connection and the flanks lie without play on the corresponding counterpieces of the recess. In principle, however, other methods for securing the tabs, such as gluing or welding, are equally conceivable, but in this case the generation of the prestress and the play-free insertion of the tabs into a possible milled-out area in the connector is more complex.

The connector is particularly preferably formed as an annular body, which surrounds the outer shaft in cross-section. In an embodiment of the invention where the catheter is inserted via an antegrade route, the connector surrounds the inner shaft in cross-section.

In accordance with a preferred embodiment of the invention, it is also provided that each tab fixed to the connector also engages in an associated recess in the connector, wherein these recesses are formed on a peripheral outer side of the connector. In accordance with one embodiment of the invention it is provided that each tab fixed to the connector preferably engages in an interlocking manner in its associated recess in the connector.

In accordance with a preferred embodiment of the invention it is also provided that the outer side, at a proximal end of the connector, includes a peripheral conical portion, such that the connector, at the proximal end of the connector, has a peripheral chamfer on the outer side, wherein those recesses for receiving the tabs are formed in the conical portion of the outer side.

In accordance with a preferred embodiment of the invention it is also provided that each recess has two flanks facing towards one another, which start from a base of the corresponding recess, wherein the recesses taper in the axial direction of the outer shaft towards the tubular portion of the capsule core, such that both flanks extend towards one another accordingly.

In accordance with a preferred embodiment of the invention it is also provided that each tab, in a state not fixed to the connector, has a curvature in the peripheral direction of the tubular portion. This curvature can correspond to the curvature of the tubular portion in the peripheral direction thereof.

In accordance with a preferred embodiment of the invention it is also provided that each tab fixed to the connector has a smaller curvature in the peripheral direction than in the state not fixed to the connector, wherein the corresponding tab fixed to the connector presses with each of its sides against an associated flank of the recess in which the tab is engaged.

In other words, each tab when fixed, in particular screwed in place, in the corresponding recess is pressed flat, thus producing the contact between the outer sides of the corresponding tab and the flanks of the associated recess.

In accordance with a preferred embodiment of the invention it is also provided that the smaller curvature does not disappear. In other words, the tabs are fixed or screwed in place in the recesses such that they are not completely pressed flat, but instead a certain residual curvature remains.

In accordance with a preferred embodiment of the invention it is also provided that the tubular portion bears against a peripheral step of the connector via edge portions extending between adjacent tabs, wherein in accordance with a preferred embodiment of the invention it is provided that the edge portions are drawn against the step by the tabs fixed to the connector. This can be ensured by the extension of the outer sides of the tabs away from one another and also the corresponding shape of the flanks, whereby the tabs are made to draw the tubular portion of the capsule core fixed thereto against the step during the fixing process In accordance with a preferred embodiment of the invention it is also provided that the tabs fixed to the connector are curved, starting from the tubular portion, towards the base of their respective associated recesses in the connector.

In accordance with a preferred embodiment of the invention it is also provided that the tabs are fixed to the connector by screws, wherein each screw engages through a through-opening in the corresponding tab and is screwed its external thread to an internal thread of an associated opening in the base of the corresponding recess.

In accordance with a preferred embodiment of the invention it is also provided that the capsule core and/or the connector are/is manufactured from a metal, in particular from a steel. In addition to stainless steel, chromium-nickel steel and also cobalt-chromium mixtures or alloys can also be used advantageously as materials in this embodiment of the invention. Nickel-titanium alloys (nitinol) or composite materials with carbon fibres are also expedient in specific embodiments.

In accordance with a preferred embodiment of the invention it is also provided that the tubular portion of the capsule core has a plurality of parallel slots running along the peripheral direction and also in particular through-openings arranged between adjacent slots. The through-openings are formed here automatically as holes created by melting in specific embodiments of the invention where the slots are produced by laser cutting in a capsule core made of metal. What are key for this embodiment, however, are the slots running in the peripheral direction. The rigidity of the capsule core can be varied by the width and frequency of the slots. Here, the rigidity of the capsule core can be varied by the width and frequency of the slots. Here, the rigidity of the capsule core is preferably increased gradually towards the transition to the connector or connector so as to ensure that the tensile and compressive stresses occurring as a result of bending load are continuously introduced into the connector or connector.

Figure 2:
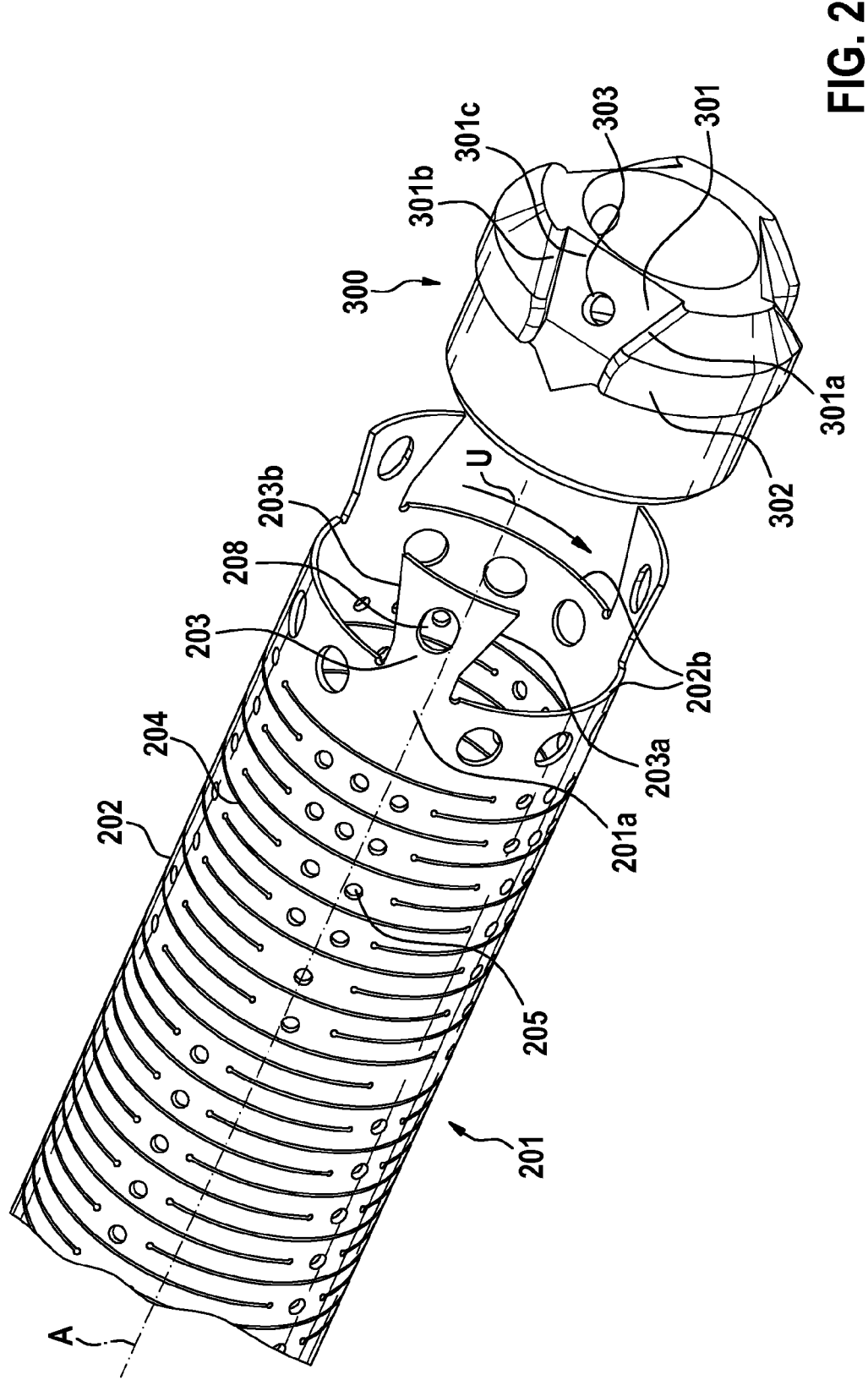
FIG. 2 shows a perspective view of a detail of a capsule core before being fixed to the connector.
Figure 3:
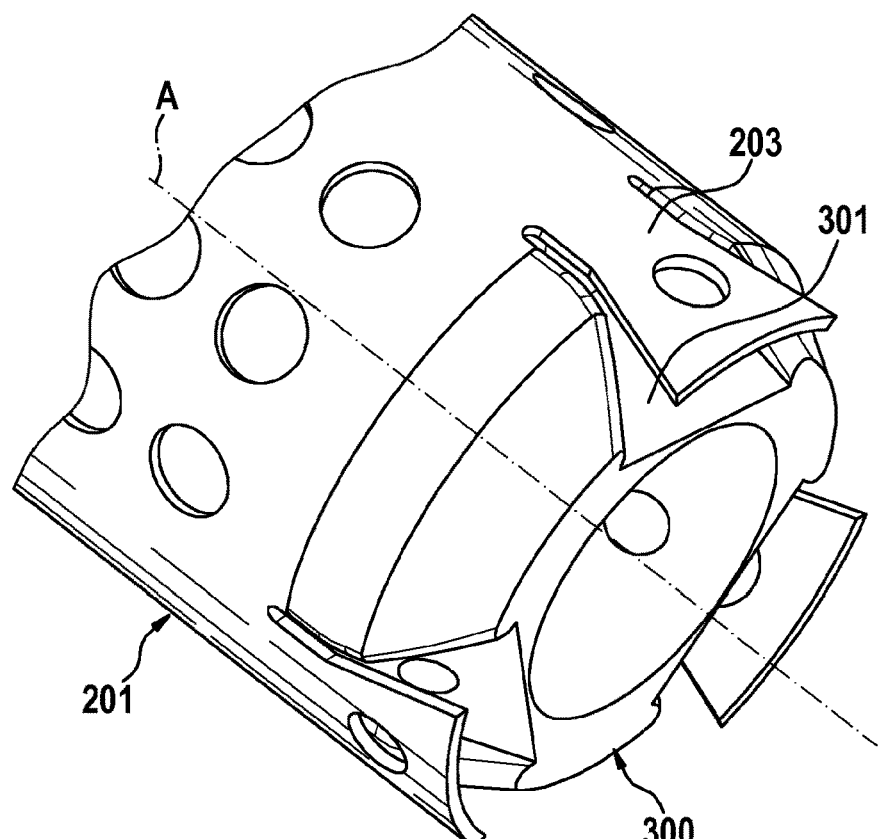
FIG. 3 shows a further perspective view of a detail of a capsule core before being fixed to the connector.
Figure 4:
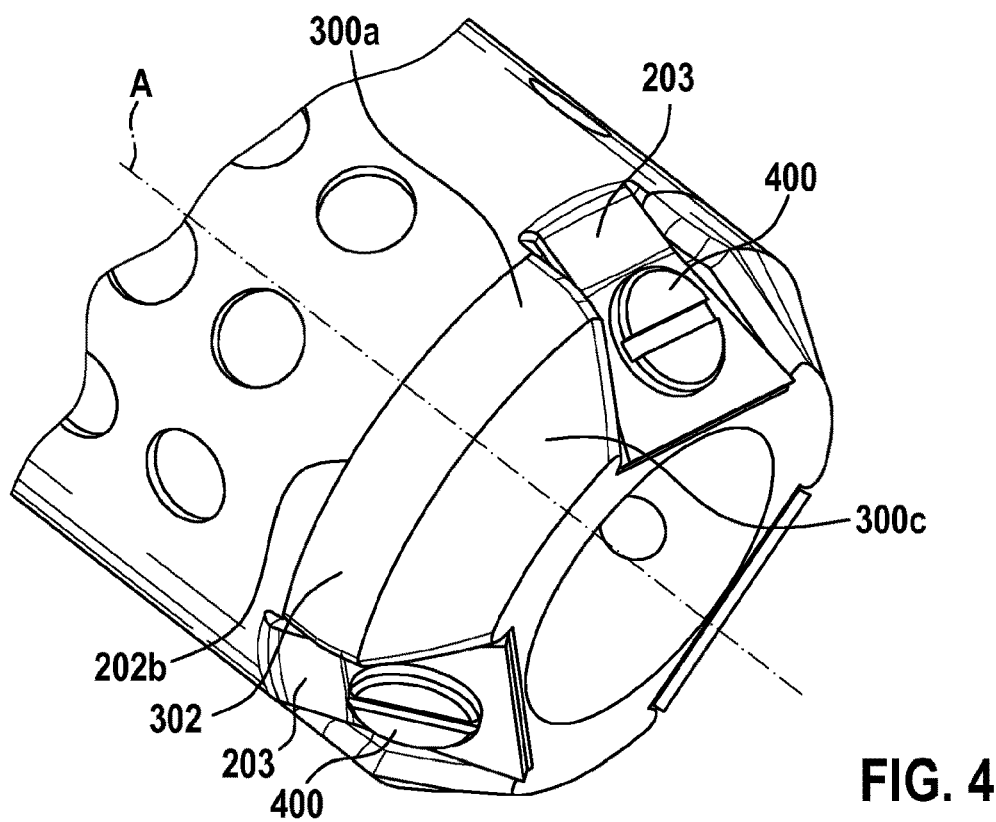
FIG. 4 shows a perspective view of a detail of a capsule core fixed to the connector.

FIG. 1 in conjunction with FIGS. 2 to 4 shows a catheter device 100 for transporting an implant I (not shown) to a target location of a body lumen of a patient. The device 100 here has an elongate inner shaft (not shown) for supporting the implant I, wherein the implant I can be fixed to a distal end of the inner shaft. The distal end of the inner shaft is opposite its proximal end, which for example can be fixed to a handle of the catheter device, by which the inner shaft and the outer shaft 5 are moved. The outer shaft 5 serves here to transport the implant to the selected target location in the body lumen of the patient. Here, the outer shaft 5 surrounds the inner shaft, such that this can be guided in the outer shaft 5 and is movable relative to the outer shaft 5 so as to move the implant, for example in the known manner, out from an implant capsule 200 fixed on the outer shaft 5, such that the implant can unfold at the target location or can be unfolded there. In this embodiment the outer shaft 5 also has a core made of a cut metal tube (also referred to as a Hypotube), which is sheathed by a polymer (not illustrated).

The implant capsule 200 has a capsule core 201 made of a metal, for example made of a steel tube, which is cut such that it has, at its proximal end 201a, continuing tabs 203, which for example form a trapezoidal end. Each tab 203 or each dovetail 203 thus has outer sides 203a and 203b facing away from one another, which extend away from one another starting from a tubular portion 202 of the capsule core 201. The capsule core 201 can also be surrounded outwardly by an outer covering or material layer 207 (also referred to as an outer jacket), wherein an inner covering or material layer 206 can be provided on the inner side of the capsule core and is also referred to as an inner liner.

The steel tube or the tubular portion 202 has a cut pattern, which for example has parallel slots 204 running in a peripheral direction U and through-openings 205 arranged between the slots 204. The cut pattern is formed here such that the rigidity of the capsule core 201 increases gradually at the transition to a connector 300, to which the tabs 203 are fixed.

It is thus ensured that the tensile and compressive stresses occurring as a result of a bending load are introduced continuously into the connector 300.

The annular connector or connector 300 preferably manufactured from a metal preferably has an outer side 300a with a conical portion 300c. Preferably three dovetail-shaped or trapezoidal recesses 301 are formed on this conical surface 300c of the cone and taper towards the distal end of the catheter device 100. The congruently shaped counterpieces in the form of the tabs 203, which are disposed on the capsule and are preferably formed integrally with a proximal end 201a of the capsule core 201, are drawn into these pockets 301, in each case by a screw 400. Here, each screw 400 engages through a through-opening 208 in the associated tab 203 and is screwed into an opening 303 provided on the base 301c of the corresponding recess 301. Since these counterpieces 203 are curved in the peripheral direction U, they are pressed flat when screwed down. As a result, the outer sides 203a, 203b of the tabs are pressed against the accordingly extending flanks or walls 301a, 301b of the recesses 301. Here, a prestressed interlocking connection is produced, which in particular is free from play. The connector 300 additionally has a peripheral step or ring 302, which serves as a stop, wherein the edge portions 201b of the tubular portion 202 of the capsule core 201 extending between the tabs 203 are drawn against the stop.

Figure 5:
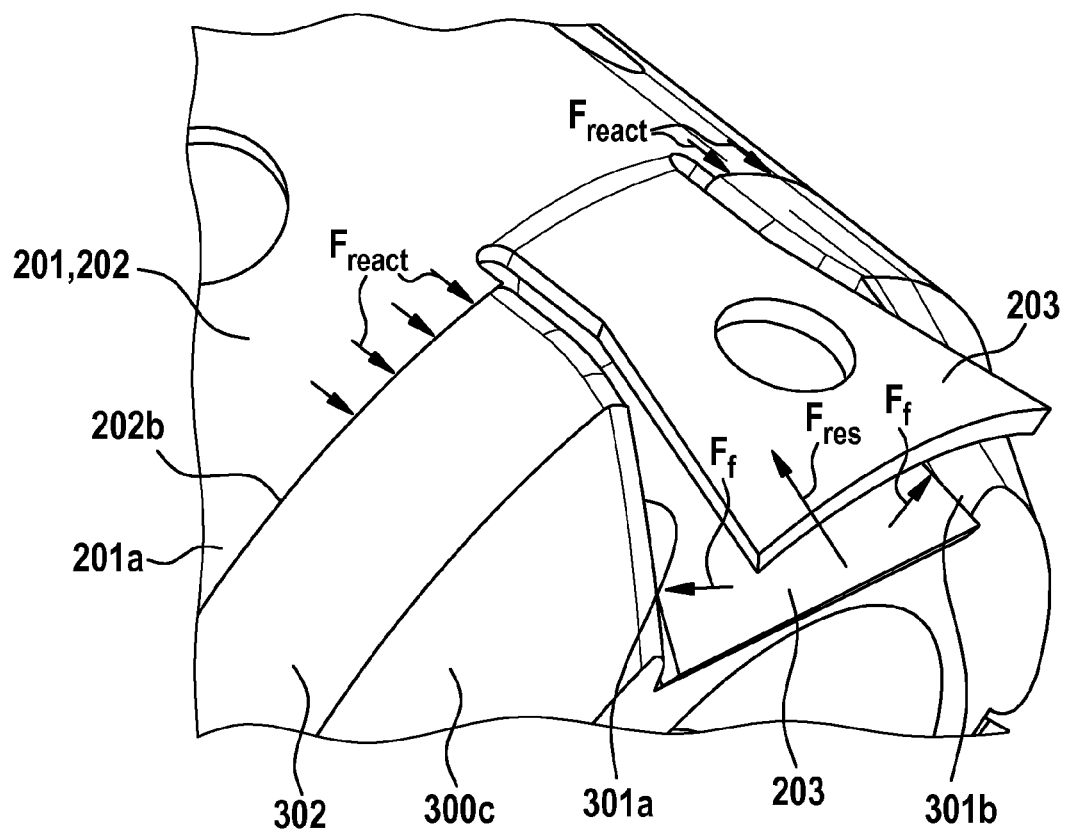
FIG. 5 shows an illustration of the forces occurring during the fixing process.

The forces occurring as the tabs 203 are fixed at the connector 300 are indicated in FIG. 5.

By pressing down the curved tab (for example dovetail) 203, this is straightened in the radial direction or peripheral direction U and presses with $F_f$ against the flanks 301a, 301b of the connector 300.

The resultant force $F_{res}$ consequently draws the capsule core 201 by its edge portions 202b against the step or stop shoulder 302 at the connector 300. The capsule core 201 presses thereagainst by the reaction forces $F_{react}$.

The geometry of the tabs and their respective counterpieces in the connector 300 (recesses 301) are selected such that the curve in the assembled state is always retained to a small extent; it can thus be guaranteed that the component parts are braced against one another and that the contact faces thus rest on one another.

The capsule 200 is connected by its load-bearing element, i.e. the capsule core 201 laser-cut from a metal tube for example, to the outer shaft in the above-described way, and thus in an interlocking and play-free manner. In accordance with one embodiment, the distal connector 300 is manufactured from a steel, wherein it is preferably welded onto the outer shaft on the catheter side. The high load-bearing capability of the steel at the connector 300 and in the capsule 200 allows a short design, which significantly reduces the rigid proportion of the catheter end. With the play-free connection to the connector 300 and an additional welding of the outer plastic coverings, it is additionally ensured that the tightness in the transition is ensured. Alternatively, an O-ring can also be used to produce the tightness (not illustrated). A further advantage of this design is that the manufacturing process does not include any injection moulding or gluing. This makes it possible for the capsule 200 to be produced using simple shrinking tubes and hot air fans by a melting method, or for the outer jacket 207 to be applied and for the inner liner 206 to be fixed to the core 201 via holes (for example 205) in the capsule core 201, the holes having been produced by melting.

The invention claimed is:

1. A catheter device for transporting an implant to a target location in a body lumen and for releasing the implant at the target location, comprising:
    an outer shaft configured to transport the implant to the target location,
    an annular connector fixed to a distal end of the outer shaft;
    an implant capsule configured to receive the implant, the implant capsule comprising a tubular capsule core that surrounds the implant prior to the release, a proximal end of the capsule core comprising a plurality of tabs for fixing the capsule core to the annular connector, wherein the tabs protrude from a tubular portion of the capsule core along an axial direction of the capsule core, the connector comprising a conical outer surface with a plurality of recesses configured to engage the plurality of tabs to draw the tubular portion of the capsule core against a stop of the connector when the plurality of tabs are pressed into the recesses.

2. The catheter device according to claim 1, wherein the plurality of tabs each have two sides extended along the axial direction, wherein the two sides extend away from one another along the axial direction starting from the tubular portion such that each tab becomes wider away from the tubular portion.

3. The catheter device according to claim 1, wherein each recess has two flanks facing towards one another, which start from a base, wherein the recesses taper along the axial direction of the outer shaft towards the tubular portion of the capsule core such that both flanks extend towards one another.

4. The catheter device according to claim 1, wherein each tab, in a natural state not fixed to the connector has a curvature in a peripheral direction of the tubular portion.

5. The catheter device according to claim 1, wherein each tab fixed to the connector has a smaller curvature in a peripheral direction than when not fixed to the connector, such that the tab presses with each of its sides against an associated flank and also a base of a recess in which the tab is engaged.

6. The catheter device according to claim 5, wherein the smaller curvature ensures that that each tab is not pressed flat when fixed to the connector.

7. The catheter device according to claim 1, wherein the tubular portion bears against a peripheral step of the connector via edge portions extending between adjacent tabs.

8. The catheter device according to claim 7, wherein the edge portions are drawn against the step by the plurality of tabs fixed to the connector.

9. The catheter device according to claim 1, wherein the plurality of tabs fixed to the connector are curved starting from the tubular portion towards a base of respective associated recesses in the connector.

10. A catheter device for transporting an implant to a target location in a body lumen and for releasing the implant at the target location, comprising:
- an outer shaft configured to transport the implant to the target location,
- an implant capsule configured to receive the implant, the implant capsule comprising a tubular capsule core that surrounds the implant prior to the release, one end of the capsule core comprising a plurality of tabs for fixing the capsule core to the outer shaft, wherein the plurality tabs protrude from a tubular portion of the capsule core along an axial direction of the capsule core,
- wherein a connector is fixed to a distal end portion of the outer shaft to fix the plurality of tabs to the outer shaft, wherein the plurality of tabs are fixed to the connector by screws.

11. The catheter device according to claim 1, wherein the capsule core and/or the connector are fabricated from a metal.

12. The catheter device according to claim 1, wherein the tubular portion of the capsule core along its axial length has a plurality of parallel slots disposed in a peripheral direction.

13. The catheter device according to claim 12, comprising through-openings arranged between adjacent ones of the plurality of parallel slots.

14. The catheter device according to claim 13, wherein the plurality of parallel slots and through-openings are configured to create gradually increasing rigidity toward the proximal end of the capsule core.

15. The catheter device according to claim 12, wherein the plurality of parallel slots are configured to create gradually increasing rigidity toward the proximal end of the capsule core.

16. The catheter device according to claim 1, wherein the capsule core is metal, and the connector is steel and has a welded connection to the distal end of the outer shaft.

17. The catheter device according to claim 1, wherein tabs of the plurality of tabs are separated from each other in a peripheral direction.

* * * * *